United States Patent [19]

Wilder

[11] 3,957,041

[45] May 18, 1976

[54] LEG ELEVATING ASSEMBLY

[75] Inventor: Joseph R. Wilder, New York, N.Y.

[73] Assignee: Michael Ebert, Mamaroneck, N.Y. ; a part interest

[22] Filed: Apr. 28, 1975

[21] Appl. No.: 572,338

[52] U.S. Cl. .................................. 128/94; 128/84 R

[51] Int. Cl.$^2$ .............................................. A61F 5/40

[58] Field of Search .................... 128/94, 83, 80, 84, 128/25, 75, 155, 156, 157, 163, 164, 165

[56] References Cited

UNITED STATES PATENTS

| | | | |
|---|---|---|---|
| 1,607,834 | 11/1926 | Line | 128/80 F |
| 2,644,448 | 7/1953 | Jardine | 128/94 X |
| 2,771,876 | 11/1956 | Scholl | 128/84 R |
| 3,149,630 | 9/1964 | Schmidt | 128/84 R |
| 3,390,675 | 7/1968 | Giannestras | 128/84 R |

*Primary Examiner*—John D. Yasko

[57] ABSTRACT

An assembly for maintaining the leg of a patient lying on a table at an elevated position thereabove to facilitate examination or treatment of the leg. The assembly is constituted by a stand having a hooked head at a height well above the table surface, and a sling formed by a loosely woven, open mesh net in a hammock-like formation, the ends of the sling having extensions terminating in rings or other couplers which are attachable to the hooked head of the stand. When the heel of the patient's foot is nested in the hammock, the net conforms to the contours of the foot to securely hold the leg in a raised position without masking the foot, whereby an antiseptic solution may be applied to the foot surface through the interstices of the net.

7 Claims, 6 Drawing Figures

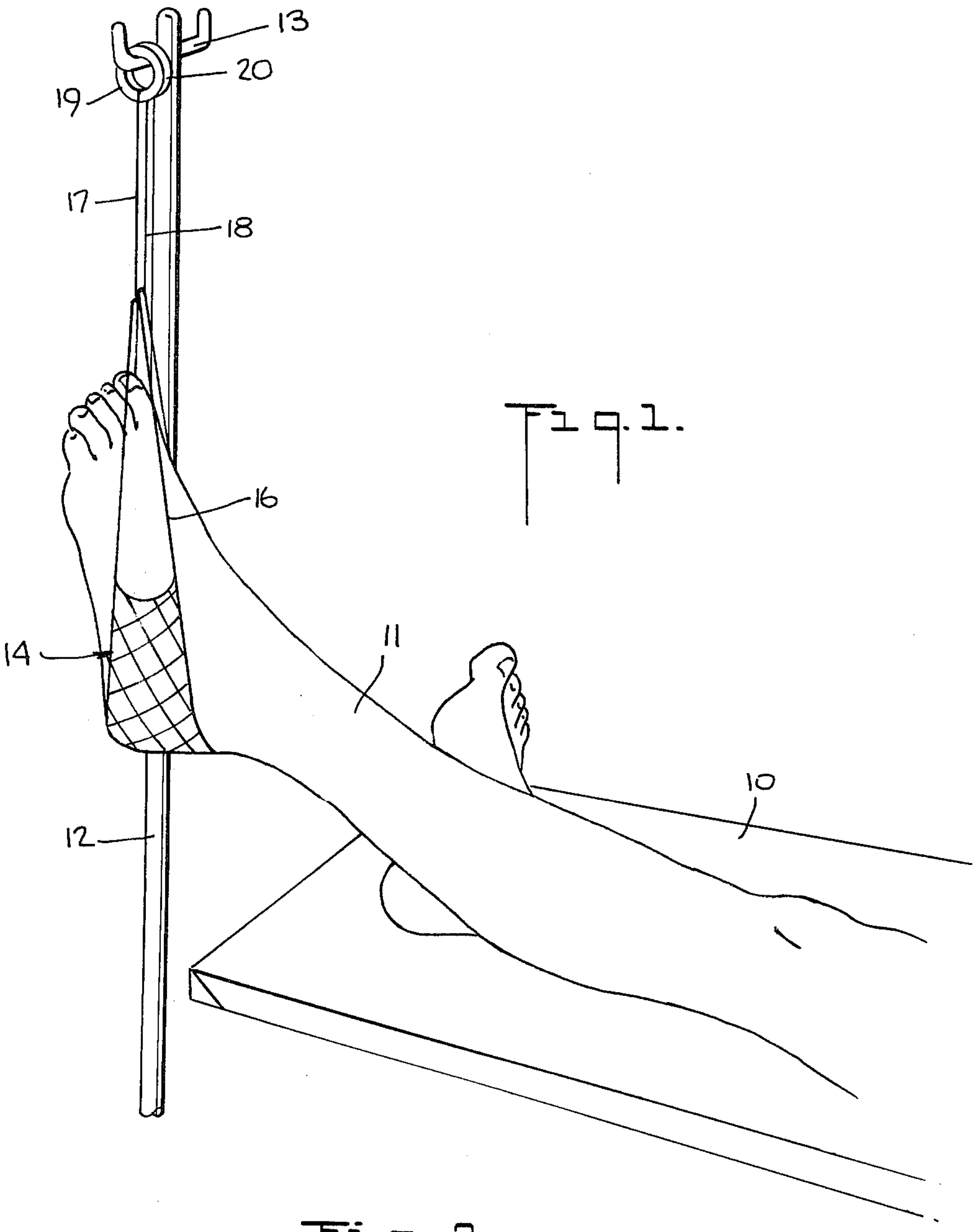
Fig. 1.
Fig. 2.
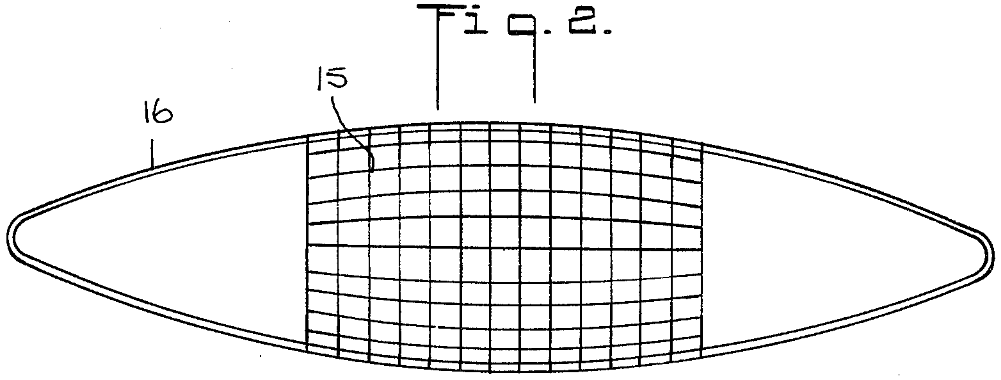

LEG ELEVATING ASSEMBLY

BACKGROUND OF INVENTION

This invention relates generally to techniques for elevating the leg of a reclining patient to facilitate examination or treatment of the leg, and more particularly to a leg elevating assembly which includes a disposable sling having a net adapted to securely engage and conform to the foot of the patient to elevate the leg without discomfort and without interfering with sterilization procedures.

There are several situations encountered in medical and surgical practice that dictate leg elevation. Thus it is sometimes necessary to elevate the leg of a patient above the surface of the table on which the patient is lying to permit a physician to freely examine, treat or dress the leg. Leg elevation is of particular importance in extremity surgery. Preparatory to such surgery, one must apply an antiseptic solution around the entire circumference of the leg from toe to groin to insure sterile conditions. This can be accomplished only by maintaining the leg in a position raised well above the table.

In existing surgical methodology, one common technique is for the surgeon, with the assistance of one or more orderlies, to prepare the leg in piecemeal fashion, the assistant holding up the leg at various points while the surgeon applies an antiseptic solution to sections of the leg. In those situations where both extremities must be prepared for surgery, this procedure often involves leg manipulations approaching the acrobatic. It also entails various leg hold-up improvisation whose effectiveness depends on the skill of the assistants. Current methods are unreliable and tiring as well as being expensive in that they are time-consuming.

It is also common practice to elevate the leg by hanging it from the big toe. This technique is crude, for it interferes with the blood supply and causes the toe to turn blue. Moreover, it is so painful to the patient that it can only be carried out when the patient is fully anaesthetized. To avoid this drawback, carriers of canvas, leather, or other strap material have been used which are adapted to engage the foot, the carrier being suspended from the head of a tall stand.

Such carriers have the serious drawback of masking the foot area engaged thereby, thereby blocking effective sterilization of the foot. Also, the edges of the carriers tend to cut into the tissue of the foot, for the positions of these edges are fixed by the predetermined shape of the carrier and do not adjust themselves to the contour of the foot.

SUMMARY OF INVENTION

In view of the foregoing, it is the main object of this invention to provide an assembly for elevating the leg of the patient, the assembly including a sling formed of a loose, open-mesh net which conforms to the contour of the foot.

Among the significant features of a mesh sling in accordance with the invention are that the sling does not interfere with the patient's blood supply, it is exceptionally comfortable, and it permits effective sterilization of the foot, for the mesh openings admit the applied antiseptic solution to the engaged foot area.

Yet another object of the invention is to provide a sling-type leg elevator which is inexpensive and disposable and which requires no particular skill to use.

Briefly stated, in an assembly in accordance with the invention, the leg is elevated by means of a tall stand whose hooked head is at a height well above the table on which the patient lies, and a sling formed of a loosely woven, open-mesh net in a hammock-like formation, the ends of the sling having cord extensions terminating in rings or other couplers which are attachable to the hooked head of the stand, whereby, when the heel of the foot is nested in the hammock, the net conforms to the contours of the foot to securely hold the leg in a raised position without masking the foot, whereby an antiseptic solution may be applied to the surface of the foot through the interstices of the net.

OUTLINE OF DRAWING

For a better understanding of the invention as well as other objects and further features thereof, reference is made to the following detailed description to be read in conjunction with the accompanying drawing, wherein:

FIG. 1 is a perspective view of a leg elevating assembly;

FIG. 2 is a plan view of the sling included in the assembly;

DESCRIPTION OF INVENTION

Figure 3:
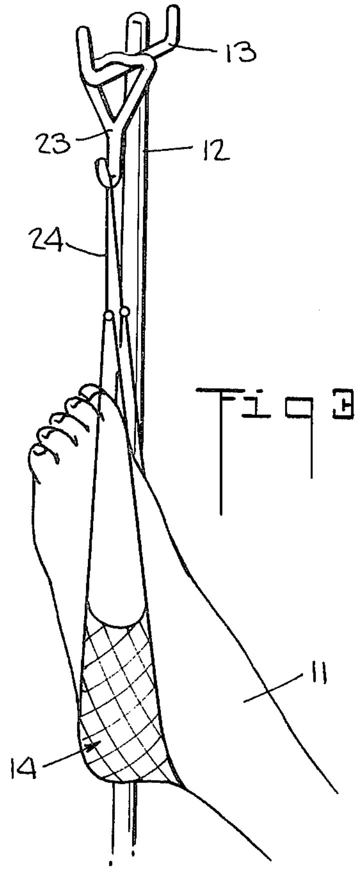
FIG. 3 is an alternative form of a sling coupler.

Referring now to FIG. 1, there is shown a patient lying on an operating table 10, the patient's left leg 11 being securely elevated above the surface of the table by an elevating assembly in accordance with the invention.

The assembly comprises a stand 12 having a hooked head 13 whose height is well above the table surface. The stand may be of telescoping construction to permit adjustment of the height of the head to a level appropriate to the height of the operating table of whatever other table the patient is placed on.

The leg is suspended from the hooked head of the stand by means of a sling, generally designated by numeral 14. Sling 14, as shown separately in FIG. 2, is formed of a loosely woven, open mesh fabric net 15 in a hammock-like formation, the perimeter of the net being reinforced by a continuous, high-strength cord 16 whose end loops provide supporting extensions for the hammock. The net is woven of sterilizable, natural or synthetic yarn of high-strength, such as cotton, nylon or polypropylene. Because of its open-mesh, loosely woven construction, the hammock tends to assume a shape conforming to the contours of the body engaged thereby.

The end loops of the sling are connected by lines 17 and 18 to metal coupling rings 19 and 20 respectively, the rings being connectable to the hooked head 13 of the stand. In practice, the sling may be approximately 18 inches long and about 3 to 5 inches wide at the center, the net tapering so that it is about 1½ to 2 inches wide at the ends.

Instead of rings as shown in FIG. 1, the sling may be coupled to the hooked head of the stand by means of a hanger 23 of the type illustrated in FIG. 3. The sling in this instance has a small loop 24 attached to its ends, the loop engaging hanger 23 so that the hanger is separable from the sling and may be reused after the sling is discarded.

Figure 4:
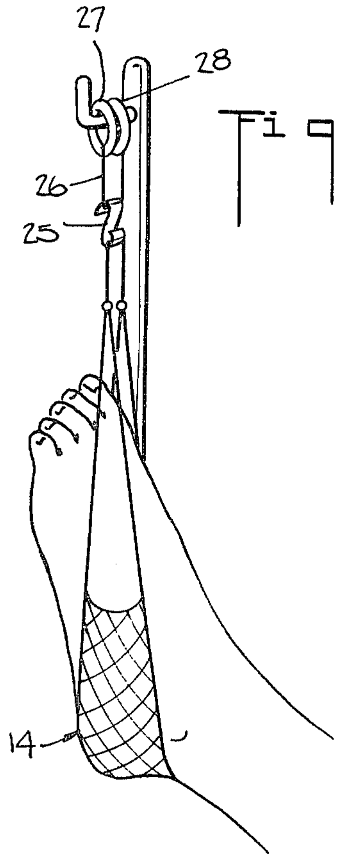
FIG. 4 is still another form of coupler.

Alternatively, as shown in FIG. 4, loop 24 of the sling may be linked to the lower section of an S-shaped connector 25 whose upper section engages a loop 26 whose ends are held to rings 27 and 28 received on the hooked-head of the stand.

Figure 5:
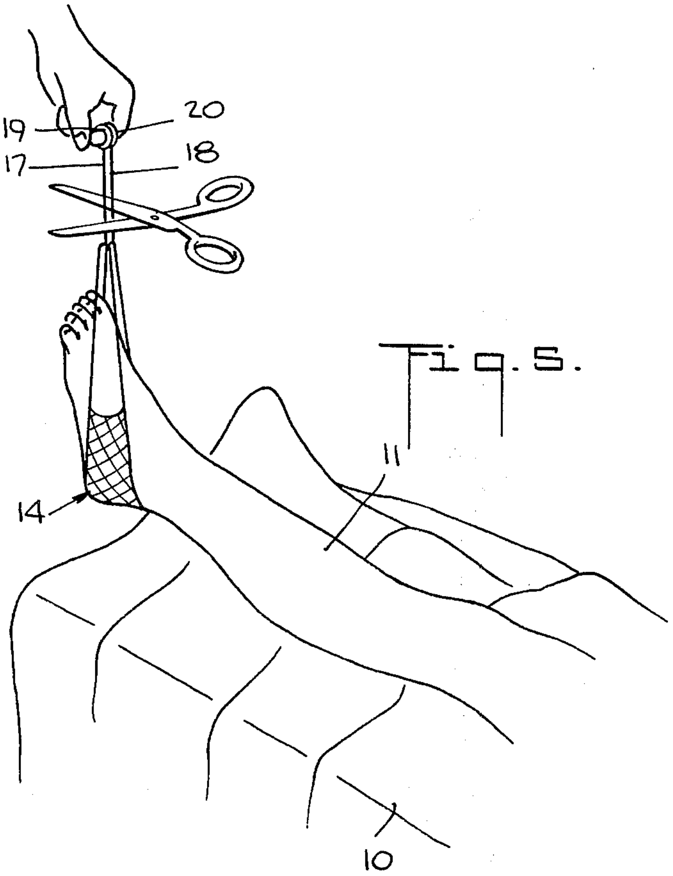
FIG. 5 illustrates the manner of lowering the leg of the patient onto the table after elevation is no longer necessary.

In practice, when using a sling of the type illustrated in FIG. 1, after the elevated leg 11 has been prepared for surgery, it may be lowered to rest on the table by the procedure illustrated in FIG. 5. Rings 19 and 20 are withdrawn from the hooked head of the stand by inserting a finger in both rings. But before lowering the prepared leg onto the table, the surface of the table and the other leg are protectively draped with sterile fabric. Then the leg is brought down, with the sling still engaging the foot of the patient. At this point, the holding rings, which are no longer sterile, are cut off by snipping the lines 17 and 18 with scissors. The use of scissors may be avoided when using an S-connection, as shown in FIG. 4. Since the sling is sterile, the fact that it remains on the table is not objectionable.

Because of the open mesh construction of the net, the surface of the foot is exposed through the interstices thereof and may be treated with an antiseptic solution preparatory to surgery. The yarns of the net are preferably formed of a material such as texturized nylon possessing wicking or capillary properties so that the solution is carried thereby to the skin in contact with the yarns. In practice, the sling, before being packaged in a suitable storage bag, is rendered sterile, so that it is ready for immediate use when removed from the bag.

Figure 6:
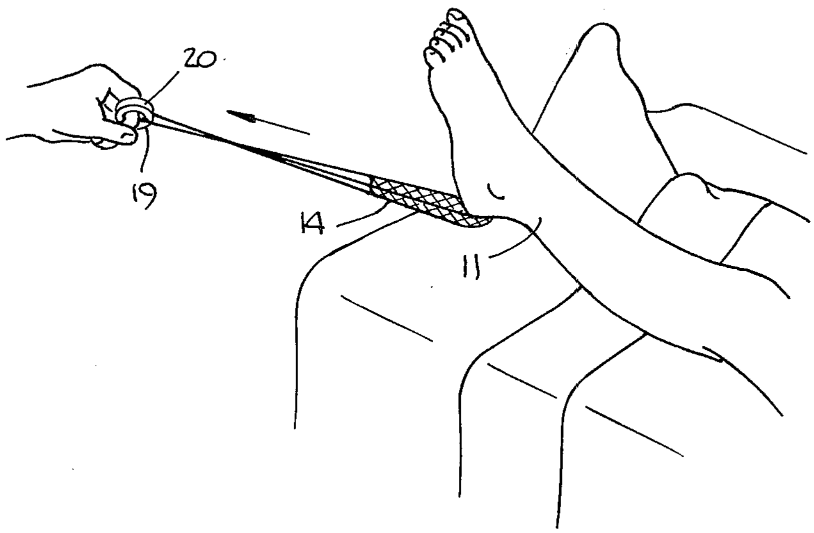
FIG. 6 illustrates a preferred manner of detaching the sling from the patient's leg.

Rather than leave the sling on the foot of the lowered leg as shown in FIG. 5, one may by means of rings 19 and 20, as shown in FIG. 6, simply pull the sling to disengage it from the foot.

While there has been shown and described preferred embodiments of a leg elevating sling assembly in accordance with the invention, it will be appreciated that many changes and modifications may be made therein without, however, departing from the essential spirit thereof.

I claim:

1. In combination with a stand having a head at a position that is raised with respect to a table, a sling for elevating the leg of a patient lying on said table to facilitate medical examination or treatment of the leg, said sling comprising a sterilizable fabric net having a open mesh formation and provided with extensions on either end thereof to define a hammock-like structure, said net being adapted to socket the heel of the patient in a nesting position in which the toes of the foot extend upwardly above the heel and without interfering with blood circulation, and means attached to the ends of the sling to engage the head of the stand, such that when the heel of the patient is nested in the net, the sling conforms to the contours of the foot to securely hold the leg in a raised position without masking the foot, whereby an antiseptic solution may be applied thereto through the interstices of the net.

2. A sling as set forth in claim 1, wherein the head of the stand is hooked, and said means is constituted by rings attached to the ends of the sling to engage the hooked head.

3. A sling as set forth in claim 1, wherein said net is formed of a loosely-woven open-mesh fabric.

4. A sling as set forth in claim 3, wherein the net is woven with yarns possessing wicking properties.

5. A sling as set forth in claim 4, wherein said yarns are made of texturized nylon.

6. A sling as set forth in claim 1, wherein the net is joined to the opposite sides of a continuous cord, whose ends provide said extensions.

7. A sling as set forth in claim 6, further including a pair of rings, each of which is connected by a line to one end of the cord.

* * * * *